US006710167B1

(12) United States Patent
Sievers et al.

(10) Patent No.: US 6,710,167 B1
(45) Date of Patent: Mar. 23, 2004

(54) PROCEDURE FOR THE CHROMATOGRAPHIC PURIFICATION OF INSULINS

(75) Inventors: Werner Sievers, Frankfurt (DE); Richard Bicker, Liederbach (DE); Dieter Desch, Frankfurt (DE); Jörg Von Eysmondt, Hofheim (DE); Reinhold Keller, Bad Soden (DE); Frank Richard, Kronberg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/379,796

(22) Filed: Aug. 24, 1999

(30) Foreign Application Priority Data

Aug. 24, 1998 (DE) .......................................... 198 38 097

(51) Int. Cl.$^7$ ............................................... C12K 14/00
(52) U.S. Cl. ...................................... 530/305; 530/303
(58) Field of Search ............................... 530/303, 305; 210/635

(56) References Cited

U.S. PATENT DOCUMENTS

| 4,616,078 | A | * | 10/1986 | DiMarchi ................... 530/305 |
| 5,245,008 | A | | 9/1993 | Dickhardt et al. ........... 530/305 |
| 5,473,049 | A | | 12/1995 | Obermeier et al. .......... 530/303 |
| 5,621,073 | A | * | 4/1997 | Dickhardt et al. ........... 530/305 |
| 5,656,722 | A | | 8/1997 | Dörschug ................... 530/303 |
| 5,663,291 | A | | 9/1997 | Obermeier et al. .......... 530/303 |

FOREIGN PATENT DOCUMENTS

| EP | 055 945 A2 | 7/1982 | ............ C12N/15/00 |
| EP | 474213 | 3/1992 | |
| EP | 547544 | 6/1993 | |
| GB | 1285024 | 8/1972 | |
| ZA | 97/6645 | 3/1998 | |

OTHER PUBLICATIONS

Krause & Bienert, "Separation of Peptides by Liquid Chromatography on Polyalkylene Columns", Journal of Liquid Chromatography 15(10), pp. 1773–1784, (1992).*

TosoHaas, "Protein & Peptide Purification and Analysis with TSK–GEL® Polymeric Reversed Phase Columns", Jul., 1997, pp. 1–4.

* cited by examiner

*Primary Examiner*—Karen Cochrane Carlson
(74) *Attorney, Agent, or Firm*—Finnegan, Henderson, Farabow, Garrett & Dunner, L.L.P.

(57) ABSTRACT

The present invention relates to an improved procedure for the chromatographic purification of insulins wherein a pressure-stable organic polymeric chromatography material is used as a stationary phase, and the mobile phase contains at least one water-miscible organic solvent and at least one buffer substance and the pH is from about 7 to about 11.

22 Claims, No Drawings

PROCEDURE FOR THE CHROMATOGRAPHIC PURIFICATION OF INSULINS

FIELD OF THE INVENTION

The present invention relates to an improved procedure for the chromatographic purification of insulins.

BACKGROUND

In addition to enzymatic and/or genetic engineering procedures, the procedures for preparing insulins essentially comprise chromatographic procedures in order to fulfill the extremely high purity demands.

The term "insulins" is understood here as meaning insulins originating from natural sources or recombinant insulins (i.e., expressed by genetically modified microorganisms) of animal or human origin (e.g., porcine insulin, bovine insulin or human insulin), proinsulins (e.g., insulin precursors, preinsulins), or insulin derivatives.

Insulin derivatives are designated below as derivatives of naturally occurring insulins, namely human insulin or animal insulins, which differ by substitution of at least one naturally occurring amino acid and/or addition of at least one amino acid and/or organic residue from the corresponding, otherwise identical naturally occurring insulin.

Human insulin is a polypeptide which is constructed of 51 amino acids. The so-called A (acidic) chain consists of 21 amino acids, and the B (basic) chain consists of 30 amino acids. In both amino acid chains, 6 cysteine residues occur, each two cysteine residues being bonded to one another via a disulfide bridge (the two chains are linked to one another by two cysteine bridges). In biologically active human insulin, the A and B chains are bonded to one another via two cysteine bridges, and a further bridge occurs in the A chain. The following cysteine residues are linked to one another in the (biologically active) human insulin:

A6–A11
A7–B7
A20–B19.

The letters A and B represent the particular insulin amino acid chain and the number represents the position of the amino acid which is counted from the amino to the carboxyl end of the respective amino acid chain.

The preparation of recombinant insulin is customarily carried out in the steps of fermentation and cell disruption, followed by protein chemistry and process technology processes, customarily chromatographic processes, for the purification of the product.

Genetic engineering procedures allow human proinsulin or proinsulin (proinsulin of insulin derivatives) which has an amino acid sequence and/or amino acid chain length differing from human insulin, to be prepared in microorganisms. The proinsulins prepared from genetically modified *Escherichia coli* cells do not have correctly bonded cysteine bridges. A procedure for obtaining human insulin having correctly bonded cysteine bridges using *E. coli* is disclosed, for example, in EP 0 055 945. Improved procedures for the preparation of human insulin and insulin derivatives having correctly bonded cysteine bridges are described in EP 0 600 372 A1 (U.S. Pat. No. 5,473,049) and in EP 0 668 292 A2 (U.S. Pat. No. 5,663,291).

Proinsulin, a precursor of insulin, prepared from genetically modified microorganisms is first isolated from the cells, correctly folded, and then converted enzymatically to human insulin. In addition to undesired by-products, the cleavage mixture obtained in the enzymatic peptidation processes contains both the valuable substance and the undesired insulin-like impurities, which do not markedly differ either in molecular weight or in other physical properties from the valuable product, thereby making separation and purification very difficult, particularly on a large industrial scale.

The process technology processes for purification are a series of various chromatography procedures (e.g., adsorption chromatography, ion-exchange chromatography, reversed phase or reverse-phase high-pressure chromatography or combinations thereof) in some cases in a number of stages using different support materials, in some cases with subsequent crystallization, the actual purification being achieved by chromatography. The removal of the insulin-like impurities in this case takes place on ion exchangers or on reversed phase silica supports.

The end-polishing (removal of very minor impurities, as the last purification stage) is customarily carried out in the high-pressure range using chromatography on reversed phase silica gel (RP-HPLC=reversed phase high-pressure liquid chromatography).

"Reversed phase silica gel" (or reverse-phase, i.e., lipophilically modified, that is hydrophobic) is understood as meaning a silica material to which a hydrophobic matrix has been applied. Examples of a hydrophobic matrix are alkanes having a chain length of 3 to 20 carbon atoms, in particular 4 to 18 carbon atoms. The particle sizes are in the range from 10 to 50 $\mu$m, the pore widths 50 to 300 Å.

Examples of chromatography procedures that, according to the prior art, utilize RP-silica gels (lipophilically modified silica gels) are EP 0 547 544 A2 (U.S. Pat. No. 5,621,073) or EP 0 474 213 A1 (U.S. Pat. No. 5,245,008). According to the prior art, the high demands on the purity of the insulins to be prepared can only be fulfilled by the use of reversed phase silica gels. The use of reversed phase silica gel, however, has crucial disadvantages:

Reversed phase silica gels are only stable in the range from pH 2 to pH 10. In the chromatography of fermentation products, high molecular weight by-products are always contained which are persistently adsorbed and cannot be desorbed using the customary elution. These by-products concentrate on the RP silica gel with time (referred to as aging of the adsorbent).

Regeneration or cleaning in place (CIP) is usually carried out only by rinsing with dilute sodium hydroxide solution. Thus, in each CIP process, a part of the RP silica gel is destroyed requiring continuous replacement which is very cost-intensive. The danger of denaturation furthermore exists for insulins on silica gels.

Many attempts have been made to replace RP gels based on silica without complete success. Attempts using RP material based on alumina or titanium dioxide (both materials are not completely pH-stable, but at least more stable than silica gel) have shown that the separation is inadequate and that the required purity cannot be achieved.

A further necessary property of chromatography materials is their pressure stability. "Pressure-stable polymeric chromatography materials" are understood as meaning particles of organic polymers, which can occur in all possible forms, e.g., rod form, fragments, or preferably, spherical form, and preferably have diameters between from about 10 μm to about 35 μm, and whose deformation under the action of pressure (up to 70 bar) is only slight. The material located in the chromatography column must be so well packed that no cavities are present (the quality of the packing determines the separation result). For the packing of columns, in principle, two different techniques are known, which can also be used in combination. The first technique is the method of compressing the packing by means of a ram that is usually hydraulically operated (DAC=direct axial compression). The second technique is a method of packing the column hydrodynamically by means of a high-pressure pump, i.e. pressing a suspension of liquid and particles into the column. In both cases, it is necessary for pressures to reach about 70 bar on the cross section of the column in order to avoid cavity formation and to pack the particles as tightly as possible.

Many organic polymer particles are not pressure-stable and deform under high pressure resulting in flat disk spheres that overlap and suppress the flow through the packing. In contrast, reversed phase silica gels are considerably more pressure-stable by nature, and barely deform under the pressures mentioned.

SUMMARY OF THE INVENTION

The object of the present invention is to provide a process for the chromatographic purification of insulins on suitable chromatography materials that are pressure-stable and can be employed in the entire pH range from about 1 to about 14. Due to the high separation efficiency of this purification process only one stage is needed.

The object is achieved by a procedure for the chromatographic purification of insulins, using a pressure-stable organic polymeric chromatography material as a stationary phase, and a mobile phase containing at least one water-miscible organic solvent and at least one buffer substance, and a pH from about 7 to about 11 during the purification stage.

Surprisingly, it was found that with chromatography in the pH range from about 7 to about 11, i.e. in the basic range, a very good separation is achieved on pressure-stable organic polymeric chromatography materials. The pH is preferably from about 9 to about 10.

A particular advantage of the procedure according to the present invention is that, in this basic pH range, the formation of the impurity deamido insulin, which is customarily formed in the acidic medium, and which, according to the specifications of insulin preparations, must be removed to very small residual amounts, is suppressed.

DETAILED DESCRIPTION

The mobile phases which are employed for the elution contain water-miscible organic solvents, for example, alcohols having 1 to 4 carbon atoms, ketones, methyl acetate or acetonitrile. Preferred alcohols are those such as 1 or 2-propanol (n or iso-propanol), methanol, or ethanol. The concentration of the water-miscible organic solvents is between from about 1 to about 90% by volume, preferably between from about 10 to about 50% by volume.

The mobile phases, furthermore, contain a buffer substance that keeps the pH of the eluent constant. Suitable buffer substances are, for example, phosphates, alkali metal or alkaline earth metal salts, such as sodium citrate or potassium acetate, ammonium citrate, acetate, sulfate or chloride.

The pH is adjusted by the addition of hydrochloric acid or sodium hydroxide solution.

The elution can be carried out isocratically, i.e., with constant concentration of the buffer substances and with a constant proportion of the organic solvent, or preferably with a linear gradient, i.e., with an increase in the proportion of solvent.

The average particle size of the pressure-stable organic polymeric chromatography material should advantageously be from about 5 μm to about 300 μm, preferably from about 10 μm to about 50 μm. The smaller the particle size, the sharper and better the separation. However, the pressure stability of smaller particles is lower.

Insulin is a relatively small polypeptide (molecular weight of about 6000) and can diffuse without problems into pores having a diameter of about 10 nm (no steric hindrance). Materials having small pore diameters are more suitable, since the specific surface area, and thus the adsorption capacity, are larger. The average pore size of the pressure-stable organic polymeric chromatography material is advantageously from about 5 nm to about 500 nm, preferably from about 10 nm to about 50 nm.

For the procedure according to the present invention, pressure-stable organic polymeric chromatography materials which preferably consist of polystyrene/divinylbenzene or of polymethacrylate are particularly suitable. Examples of commercially available pressure-stable organic polymeric chromatography materials which can be advantageously employed in the procedure according to the present invention are compiled in Table 1.

TABLE 1

Commercially available chromatography materials

| Manufacturer | Trade name | Material | Smallest particle size [μm] | Pore diameter [nm] |
| --- | --- | --- | --- | --- |
| TosoHaas | AMBERCHROME ® | PMA | 35 | 100 |
| Pharmacia | SOURCE ® | StDVB | 15 | 100 |
| Perseptive | POROS ® | StDVB | 10 | 200 |
| Mitsubishi | CHP20P ® | StDVB | 35 | 100 |
| Biosepra | RPC POLYBIO ® | StDVB | 10 | 30 |
| Macherey & Nagel | NUCLEOGEL ® | StDVB | 20 | 10 |

TABLE 1-continued

Commercially available chromatography materials

| Manufacturer | Trade name | Material | Smallest particle size [μm] | Pore diameter [nm] |
|---|---|---|---|---|
| Polymer Laboratories | PLRP ® | StDVB | 10–15 | 10 |

PMA = polymethacrylate
StDVB = styrene/divinylbenzene

The procedure according to the invention is suitable for analytical, for semipreparative, and in particular, for preparative chromatography. The term "preparative chromatography" is understood as meaning the preparation of pure products on a technical scale.

Prior to the discovery of the present invention, in order to achieve the purity necessary for insulin preparations, it was necessary to include at least one additional reversed phase chromatography or cation exchange chromatography step and, if appropriate, a crystallization step before the reversed phase chromatography (for example, see EP 0 547 544 A2 (U.S. Pat. No. 5,621,073) or EP 0 474 213 A1 (U.S. Pat. No. 5,245,008)). In the procedure according to the invention, the same result is achieved with a single stage chromatography on the polymer support. Using the procedure according to the invention, the total yield in the insulin preparation is therefore significantly improved, as losses in yield are eliminated by combining several process stages into one stage.

The procedure according to the present invention is suitable for the chromatographic purification of all insulins according to the definition introduced at the outset, namely insulins originating from natural sources or recombinant insulins (i.e., expressed by genetically modified microorganisms) of animal or human origin (e.g., porcine insulin, bovine insulin or human insulin), proinsulins (e.g., insulin precursors, preinsulins), or insulin derivatives, insulin derivatives being understood as meaning derivatives of naturally occurring insulins, namely human insulin or animal insulins, which differ from the corresponding, otherwise identical naturally occurring insulin by substitution of at least one naturally occurring amino acid residue and/or addition of at least one amino acid residue and/or organic residue.

Examples of such insulins are human insulin, bovine insulin, porcine insulin, insulins according to EP 0 368 187 (U.S. Pat. No. 5,656,722), for example Gly(A21), Arg(B31), Arg(B32) human insulin, insulins according to EP 0 821 006 (ZA 97/6645) or the insulins described in EP 0 547 544 A1 (U.S. Pat. No. 5,621,073), EP 0 474 213 A1 (U.S. Pat. No. 5,245,008), EP 0 600 372 A1 (U.S. Pat. No. 5,473,049) or in EP 0 668 292 (U.S. Pat. No. 5,663,291). (The letters A and B represent the respective insulin amino acid chain, the number for the position of the naturally occurring amino acid residue, which is replaced by the amino acid residue given before the brackets.)

EXAMPLES

Example 1

Variation of the pH

In Example 1, tests were done on a 10 mm (diameter) by 120 mm (length) semipreparative column packed with 10–15μm 100A PLRP-S (Polymer Laboratories). The object was to purify prepurified insulin which has a purity of 95 area % in such a way that the purity was greater than 98.5 area %.

The amount applied was adjusted such that loading of the polymer chromatography material resulted in a bed volume of 6 g/liter. The application buffer and the mobile phase were water/propanol mixtures, containing 0.05 M ammonium acetate and 0.1 M glycine, which were adjusted to the respective pH using hydrochloric acid or NaOH. The empty tube rate was 150 cm/h. The three pH values, pH 3.5–pH 6.8–pH 9 were adjusted. The eluate was collected in fractions.

Table 2 shows the results. Purities above 98 area % are achieved only at pH 9, and the specifications are thus fulfilled. It can be clearly seen that insulin purification on polymeric chromatography materials only has the required efficiency in the basic medium.

TABLE 2

Purity and concentration of insulin at different pH values using the polymer chromatography material 10–15 μm 100 A PLRP-S

| | pH 3.5 | | pH 6.8 | | pH 9 | |
|---|---|---|---|---|---|---|
| Fraction | Purity [area %] | Conc. [mg/ml] | Purity [area %] | Conc. [mg/ml] | Purity [area %] | Conc. [mg/ml] |
| 1 | | | 95.22 | 0.236 | 92.74 | 0.565 |
| 2 | 96.74 | 0.449 | 94.68 | 0.196 | 96.70 | 1.310 |
| 3 | 96.69 | 0.690 | 94.84 | 0.274 | 98.59 | 1.362 |
| 4 | 97.43 | 1.020 | 95.38 | 0.454 | 99.54 | 2.020 |
| 5 | 97.39 | 1.240 | 96.84 | 1.120 | 98.99 | 2.230 |
| 6 | 97.14 | 1.330 | 97.95 | 2.236 | 99.24 | 1.730 |
| 7 | 96.07 | 1.250 | 97.82 | 3.140 | 98.80 | 1.340 |
| 8 | 94.94 | 1.120 | 97.64 | 3.120 | 98.46 | 1.200 |
| 9 | 93.30 | 0.974 | 97.12 | 2.080 | 97.28 | 0.960 |

Example 2

Pressure Stability and Packing of a Column

A chromatography column (PROCHROM® D LC50, of 50 mm diameter) was packed using the DAC (Direct Axial Compression) technique. The chromatography material (stationary phase) was introduced into 100% methanol and packed into the column. The pressure loss of an 11% propanol mixture was measured at various flow rates. The tamping pressure of the chromatography column was varied between about 5 and about 80 bar. The following chromatography materials were investigated:

PLRP-S 10-15 100® (Polymer Laboratories)
SOURCE® 15 RPC (Amersham Pharmacia Biotech)
KROMASIL® 13-120 (Akzo Nobel)

The materials have approximately identical particle diameters (spherical particles). PLRP® and SOURCE® are polymers; KROMASIL® is a high-grade RP-silica gel.

TABLE 3

| | Tamping pressure 5 bar | | Tamping pressure 20 bar | | Tamping pressure 40 bar | | Tamping pressure 80 bar |
|---|---|---|---|---|---|---|---|
| cm/h | PLRP® | SOURCE® | PLRP® | SOURCE® | PLRP® | SOURCE® | KROMASIL® |
| 50 | 0.31 | 0.40 | 0.32 | 0.85 | 0.50 | 3.33 | 0.5 |
| 100 | 0.62 | 0.80 | 0.72 | 1.85 | 1.08 | 6.33 | 1.0 |
| 150 | 1.00 | 1.50 | 1.04 | 3.14 | 1.67 | 9.33 | 1.6 |

Pressure loss in [bar/cm] of a propanol/water mixture

A specific pressure loss of 1 bar/cm means a pressure fall of 30 bar in a 30 cm high packing, which is customary in technical chromatography.

Example 3
Purification of Human Insulin on the Preparative Scale

A total of 3 examples are described below, in which human insulin is purified in a technical column that is packed according to the DAC principle using a movable ram. A PROCHROM® column, type LC50, was used. For all experiments, the packing in each case has identical dimensions of 50 mm diameter and, bed length from about 110 mm to about 120 mm.

The purpose of the experiment was to bring human insulin having a purity of about 95 area % to a purity of greater than about 98.5 area %.

Three chromatography supports were used:
PLRP-S 10-15 100® (Polymer Laboratories)
SOURCE® 15 RPC (Amersham Pharmacia Biotech)
KROMASIL® C4 13-120 (Akzo Nobel)

As already described in Example 2, PLRP and SOURCE® are polymer materials, while KROMASIL® is a high-grade RP silica gel support.

The application buffer and the mobile phase correspond to the details in Example 1. The loading is indicated in grams of human insulin per liter of bed volume. Yield is understood as meaning the proportion of the eluate which has a purity of greater than about 98.5 area %.

TABLE 4

Yield in the preparative purification of human insulin

| Support | Loading | pH | Tamping pressure | Yield |
|---|---|---|---|---|
| PLRP-S 10–15 100 ® | 6 g/L BV | 9 | 40 bar | 60% |
| SOURCE ® 15 RPC | 6 g/L BV | 9 | 25 bar | 73% |
| KROMASIL ® C4 13-120 | 6 g/L BV | 3.5 | 80 bar | 68% |

The yields achieved are compared in Table 4. The values of 60 to 70% are surprisingly good for a bed length of about 12 cm. The crucial difference between the prior art (purification using a silica gel support, in this case KROMASIL®) and chromatography using a polymer support is the pH difference: yields of this level can only be achieved at a pH of 9.

Example 4
Purification of Bolus Insulin on the Preparative Scale

In this example, a bolus insulin (fast-acting insulin) was to be purified. The example was moreover intended to demonstrate that even relatively poor qualities are permissible as starting conditions for this chromatography stage. The prior art teaches that the final purification of insulin is customarily carried out in two chromatography stages. If the end-polishing stage is directly loaded with a poor, i.e. severely contaminated material, the required purities and high yields can not be achieved at the same time.

Surprisingly, it was now found that the polymer material investigated achieved this purity in a single chromatography step, which can be attributed to the small particle diameter of from about 10 $\mu$m to about 15 $\mu$m and the excellent adsorption properties.

Four tests were made, with the following starting conditions:

75 area % purity
85 area % purity
89 area % purity
93 area % purity

In Table 5, the yields achieved (i.e., that proportion of the insulin employed which was eluted with a purity of greater than about 98.5 area %) are compiled. It can be seen that if the starting condition had only 75 area %, a purity of above 98.5 area % was not achieved. The purity was in the range of only 98.0 area %.

However, if the starting conditions were above 85 area %, the required purities of greater than 98.5% were reliably achieved, with yields between 60 and 80%.

The preparative conditions were as described in Example 1. All tests were carried out in a PROCHROM® column type LC50 of 50 mm diameter and 12 cm packing height. The loading was 6 g/l of BV in each case, the pH was adjusted to 9, and the tamping pressure was measured at 35 bar.

TABLE 5

Purification of bolus insulins of various qualities

| Support | Purity of the starting condition in area % | Yield (purity greater than 98.5 area %) |
|---|---|---|
| PLRP-S 10–15 100 ® | 75 area % | 0% |
| PLRP-S 10–15 100 ® | 85 area % | 64% |
| PLRP-S 10–15 100 ® | 89 area % | 73% |
| PLRP-S 10–15 100 ® | 93 area % | 73% |

With the aid of Table 5 it can be readily seen how the yield in the chromatography increases depending on the quality of the starting condition. The tests clearly show that the purification is achievable in a single chromatography stage.

We claim:

1. A procedure for the end-polishing of an insulin in an insulin purification process, comprising the steps of:
   a) obtaining a sample containing an insulin of at least 85 area % purity, and
   b) purifying said insulin using a stationary phase and a mobile phase, wherein the stationary phase comprises a pressure-stable organic polymeric chromatography material and the mobile phase comprises at least one water-miscible organic solvent and at least one buffer substance, and wherein, the pH is from 7 to about 11; wherein said procedure end-polishes said insulin.

2. The procedure as claimed in claim 1, wherein the pH is between from about 9 to about 10.

3. The procedure as claimed in claim 1, wherein the water-miscible organic solvent is an alcohol having 1 to 4 carbon atoms.

4. The procedure as claimed in claim 3, wherein the alcohol is 1-propanol or 2-propanol.

5. The procedure as claimed in claim 3, wherein the alcohol is ethanol.

6. The procedure as claimed in claim 3, wherein the alcohol is methanol.

7. The procedure as claimed in claim 2, wherein the water-miscible organic solvent is a ketone.

8. The procedure as claimed in claim 2, wherein the water-miscible organic solvent is methyl acetate.

9. The procedure as claimed in claim 2, wherein the water-miscible organic solvent is acetonitrile.

10. The procedure as claimed in claim 1, wherein the concentration of the water-miscible organic solvent in the mobile phase is from about 1% to about 90% by volume.

11. The procedure as claimed in claim 10, wherein the concentration of the water-miscible organic solvent in the mobile phase is from about 10% to about 50% by volume.

12. The procedure as claimed in claim 1, wherein the elution is carried out isocratically.

13. The procedure as claimed in claim 1, wherein the elution is carried out using a linearly increased gradient of the proportion of the water-miscible organic solvent.

14. The procedure as claimed in claim 1, wherein the pressure-stable organic polymeric chromatography material has an average particle size of from about 5 $\mu$m to about 300 $\mu$m.

15. The procedure as claimed in claim 14, wherein the average particle size is from about 10 $\mu$m to about 50 $\mu$m.

16. The procedure as claimed in claim 1, wherein the average pore size of the pressure-stable organic polymeric chromatography material is from about 5 nm to about 500 nm.

17. The procedure as claimed in claim 16, wherein the average pore size is from about 10 nm to about 50 nm.

18. The procedure as claimed in claim 1, wherein the pressure-stable organic polymeric chromatography material consists of a polymethacrylate.

19. The procedure as claimed in claim 1, wherein the pressure-stable organic polymeric chromatography material consists of a polystyrene/divinylbenzene.

20. A procedure for the end-polishing of an insulin in an insulin purification process, comprising the steps of:
    a) obtaining a sample containing an insulin of at least 85% area purity;
    b) preparing a stationary phase under pressure, wherein said stationary phase comprises a pressure-stable organic polymeric chromatography material, and wherein said pressure ranges from 5 bar to 80 bar; and
    c) purifying said insulin using said stationary phase and a mobile phase, wherein said mobile phase comprises at least one water-miscible organic solvent and at least one buffer substance, and wherein, the pH is from 7 to about 11;
    wherein said procedure end-polishes said insulin.

21. The procedure according to claim 20, wherein the pressure ranges from 25 bar to 80 bar.

22. The procedure according to claim 20, wherein the pressure is 35 bar.

* * * * *